United States Patent [19]

Furutaka et al.

[11] Patent Number: 5,688,379
[45] Date of Patent: Nov. 18, 1997

[54] PROCESS FOR PREPARING PERFLUOROALKYL BROMIDES

[75] Inventors: Yasuhisa Furutaka; Tatsuo Nakada; Kazuhiro Shimokawa; Yorisato Hisanaga; Souichi Ueda, all of Settsu, Japan

[73] Assignee: Daikin Industries, Ltd., Osaka, Japan

[21] Appl. No.: 424,518

[22] PCT Filed: Nov. 30, 1993

[86] PCT No.: PCT/JP93/01738

§ 371 Date: Oct. 24, 1995

§ 102(e) Date: Oct. 24, 1995

[87] PCT Pub. No.: WO94/12453

PCT Pub. Date: Jun. 9, 1994

[30] Foreign Application Priority Data

Nov. 30, 1992 [JP] Japan .................. 4-345303

[51] Int. Cl.[6] .................. C07C 17/00; C07C 17/20
[52] U.S. Cl. .................. 204/157.95; 204/158.11; 204/158.12; 570/170
[58] Field of Search .................. 204/157.15, 157.6, 204/157.95, 158.11, 158.12; 570/170

[56] References Cited

U.S. PATENT DOCUMENTS 5,051,535 9/1991 Von Werner .................. 570/170

FOREIGN PATENT DOCUMENTS 40 37 169 5/1992 Germany.

*Primary Examiner*—Kathryn L. Gorgos
*Assistant Examiner*—Edna Wong
*Attorney, Agent, or Firm*—Nikaido, Marmelstein, Murray & Oram LLP

[57] ABSTRACT

The present invention provides a process for preparing a perfluoroalkyl bromide characterized by reacting a perfluoroalkyl iodide represented by the formula $C_nF_{2n+1}I$ wherein n is an integer of 6 to 10 with bromine in a light-transmitting reactor with exposure to light and heating at 120° to 180° C. while simultaneously removing IBr resulting as a by-product by separation of a layer.

5 Claims, 3 Drawing Sheets

PROCESS FOR PREPARING PERFLUOROALKYL BROMIDES

This is a national stage application of PCT/JP93/01738 filed Nov. 30, 1993.

TECHNICAL FIELD

The present invention relates to an efficient process for preparing perfluoroalkyl bromides. Perfluoroalkyl bromides are capable of providing a contrast in X-ray radiography and MR imaging, and are compounds useful as base materials for such diagnostic chemicals. Advanced contrast media for X-ray radiography and MR imaging have been developed especially from perfluorooctyl bromide.

BACKGROUND ART

To our knowledge, heat and light effect bromination perfluoroalkyl iodides with bromine, whereas we have found that this reaction requires a high temperature of at least 300° C. when to be effected thermally with a high efficiency, or takes a long period of time when light is used for the progress of the reaction since IBr formed as a by-product blocks light.

Although the thermal reaction proceeds over a wide temperature range of 40° to 500° C., the reaction must be conducted in the presence of a radical initiator (JP-A784033/1985) or at a high temperature of not lower than 300° C. (JP-A-287551/1991) if perfluoroalkyl bromides are to be prepared efficiently. When the reaction is to be conducted at such a high temperature, however, the reactor and the piping therefor need to be made of a material which is resistant to pressure and to corrosion with bromine.

On the other hand, a report was made to the effect that a perfluoroalkyl bromide was available when a perfluoroalkyl iodide and bromine were irradiated, as enclosed in a glass tube, with ultraviolet rays for 7 days [R. N. Haszeldine, J. Chem. Soc., 3761–3768 (1953)], whereas the reaction is on an experimental scale, requires a long period of time and therefore appears industrially infeasible. Thus, preparation of perfluoroalkyl bromides from perfluoroalkyl iodides and bromine necessitates a long period of time in the case of the photoreaction, or a radical initiator or high temperature in the case of the thermal reaction.

An object of the present invention is to provide a process for industrially advantageously preparing a perfluoroalkyl bromide under a mild heating condition efficiently within a short period of time and in a high yield without using a radical initiator or like additive.

DISCLOSURE OF THE INVENTION

The present invention provides a process for preparing a perfluoroalkyl bromide characterized by reacting a perfluoroalkyl iodide represented by the formula (n:6~10) with bromine in a light-transmitting reactor with exposure to light and heating at 120° to 180° C. while simultaneously removing IBr resulting as a by-product by separation of a layer.

The perfluoroalkyl iodide represented by the above formula and to be used as the starting material in the present invention may be a straight-chain or branched compound. Examples of such iodides are $CF_3(CF_2)_5I$, $(CF_3)_2CF(CF_2)_4I$, $CF_3(CF_2)_6I$, $CF_3(CF_2)_7I$ and the like. In the above formula, n is more preferably in the range of 6 to 8. Preferably, the ratio between the reactants is, for example, about 1 to about 3 moles of bromine per mole of the perfluoroalkyl iodide.

Although the reaction is conducted by placing the starting material, i.e., perfluoroalkyl iodide, into a light-transmitting reactor and adding bromine dropwise to the iodide with heating and exposure to light, a small amount of bromine may be added to the material before the reaction. The reaction can be carried out also in a continuous mode. FIG. 2 is a flow chart showing the continuous mode. Usable as the light-transmitting reactor is, for example, a flask or tube made of glass or other reactor made of glass. The reaction temperature is preferably 120° to 180° C. at which the perfluoroalkyl iodide generally refluxes, more preferably 140° to 160° C. If lower than the above-mentioned lower limit, the reaction temperature is lower than the boiling point of IBr at atmospheric pressure, making it impossible to remove IBr and consequently resulting in a greatly reduced reaction velocity. If the temperature is higher than the upper limit, the reaction system becomes difficult to handle owing to vigorous reflux. Usable as the light are visible rays, and rays, such as ultraviolet rays, which are up to 1 μm, preferably 0.2 to 0.7 μm, in wavelength. Furthermore, decomposition of the material is avoidable effectively by conducting the reaction in a nitrogen stream.

The IBr formed as a by-product by the present process is approximate to the starting material, perfluoroalkyl iodide, and the desired product, perfluoroalkyl bromide, in boiling point, and was difficult to separate from the starting material and the desired product by distillation only. However, we have found that when the mixture of IBr, starting material and desired product is allowed to stand, the IBr separates in the form of a lower layer since IBr is sparingly soluble in the starting material and the desired product and greater than the material and the product in specific gravity. Accordingly, when the reactor has a reflux tube provides at a lower portion thereof with a trap for separating a layer, the IBr separates in the form of a lower layer and can be withdrawn continuously during the reaction by drawing off the IBr from a lower portion of the trap. The withdrawal of light-blocking IBr from the reaction system in the form of a separate layer permits the light to achieve an improved reaction efficiency, and is advantageous also in increasing the concentration of the starting material.

As described above, the present invention attains an improved reaction efficiency and affords the desired product in a high yield within a short period of time by continuously withdrawing from the system the by-product of IBr as separated in the form of a layer. After the completion of the reaction, the desired product, i.e., a perfluoroalkyl bromide, can be obtained readily, for example, by washing the reaction mixture with an alkali or reducing agent and subsequently rectifying the mixture.

BEST MODE OF CARRYING OUT THE INVENTION

The present invention will be described with reference to the following examples.

EXAMPLE 1

Figure 1:
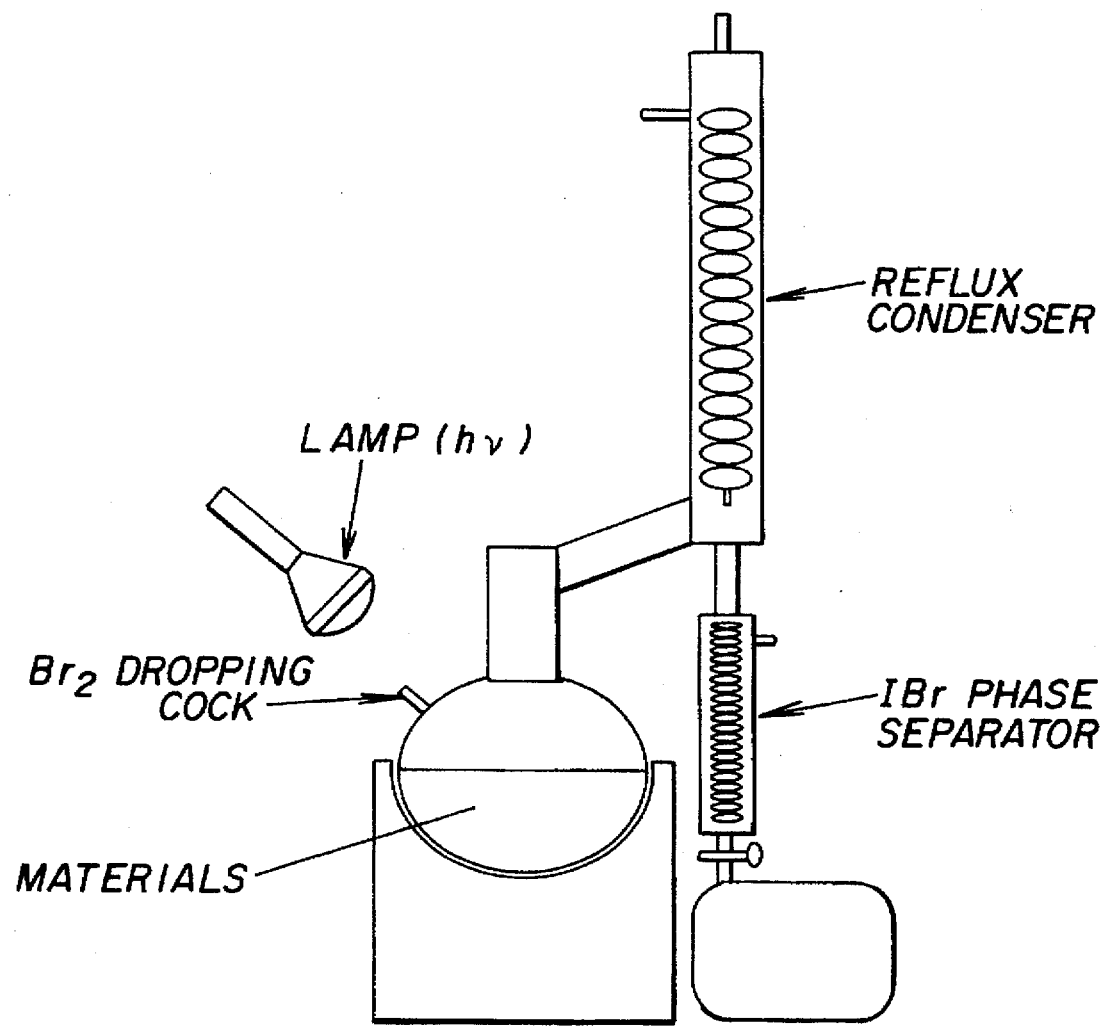
FIG. 1 shows an example of a reactor adapted for continuous withdrawal of IBr for use in the invention.
Figure 2:
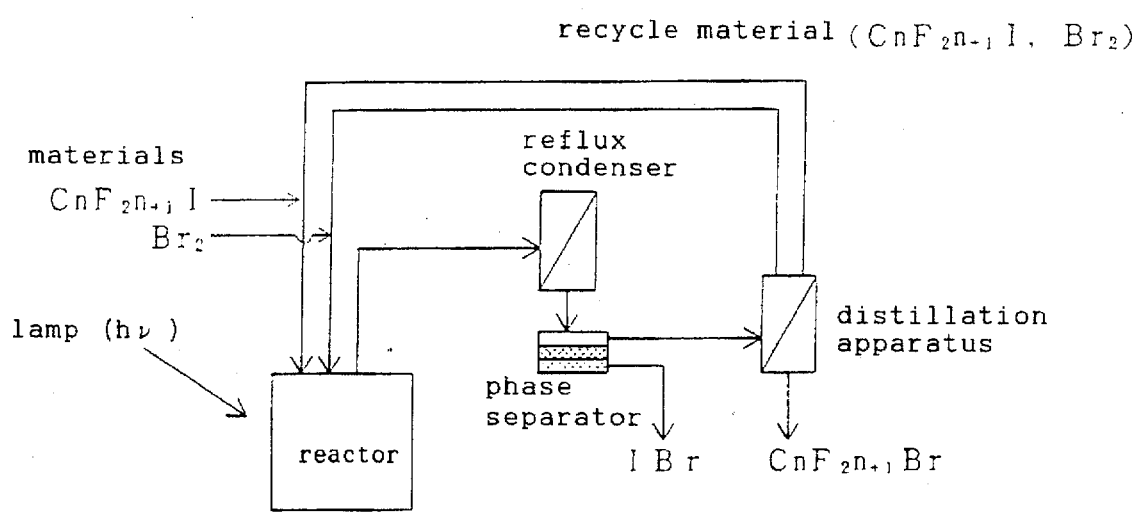
FIG. 2 is an example of flow chart of a continuous reaction for use in the invention.

With reference to FIG. 1, and H-shaped tube equipped with a Dimroth condenser and a Dimroth condenser having an IBr withdrawing cock was attached to a 500-ml four-necked flask. Into the flask were placed 200 ml (747 mM) of perfluorooctyl iodide (PFOI) and 5.0 ml (97.1 mM) of bomine, and the mixture was heated at 150° to 155° C. and irradiated with a 500-W visible light lamp. After the reaction mixture started to reflux, 49.5 ml (972 mM) of bromine was added dropwise to the mixture at a rate of 0.2 ml/min over a period of about 4 hours. The resulting IBr was drawn off at a suitable time through the IBr withdrawing Dimroth condenser. The reaction was continued for 5 hours, and the reaction mixture was thereafter cooled and washed with a 5% aqueous solution (200 ml) of sodium hydroxide to obtain 344.9 g (92.5% in yield) of perfluorooctyl bromide.

EXAMPLE 2

The same reactor as in Example 1 was used. Into the flask was placed 200 ml (747 mM) of perfluorooctyl iodide (PFOI), which was then heated at 160° C. and irradiated with a 400-W high-pressure mercury lamp. After the reaction mixture started to reflux, 54.5 ml (1.07M) of bromine was added dropwise to the mixture at a rate of 0.4 ml/min over a period of about 2 hours. The resulting IBr was drawn off at a suitable time through the IBr withdrawing Dimroth condenser. The reaction was continued for 3 hours, and the reaction mixture was thereafter cooled and washed with a 5% aqueous solution (200 ml) of sodium hydroxide, giving 349.0 g (93.6% in yield) of perfluorooctyl bromide.

Comparative Example 1

A reaction was conducted in the same manner as in Example 1 except that no IBr was withdrawn, consequently giving perfluorooctyl bromide ($C_8F_{17}Br$) in a yield of 12%.

Comparative Example 2

A reaction was conducted in the same manner as in Example 2 except that no IBr was withdrawn, consequently giving perfluorooctyl bromide ($C_8F_{17}Br$) in a yield of 19%.

Comparative Example 3

A reaction was conducted in the same manner as in Example 1 with the exception of withdrawing no IBr and using not light for irradiation, consequently giving perfluorooctyl bromide ($C_8F_{17}Br$) in a yield of 4%.

Comparative Example 4

A reaction was conducted in the same manner as in Example 1 except that the reaction temperature was 110° C., consequently giving perfluorooctyl bromide ($C_8F_{17}Br$) in a yield of 5M.

Figure 3:
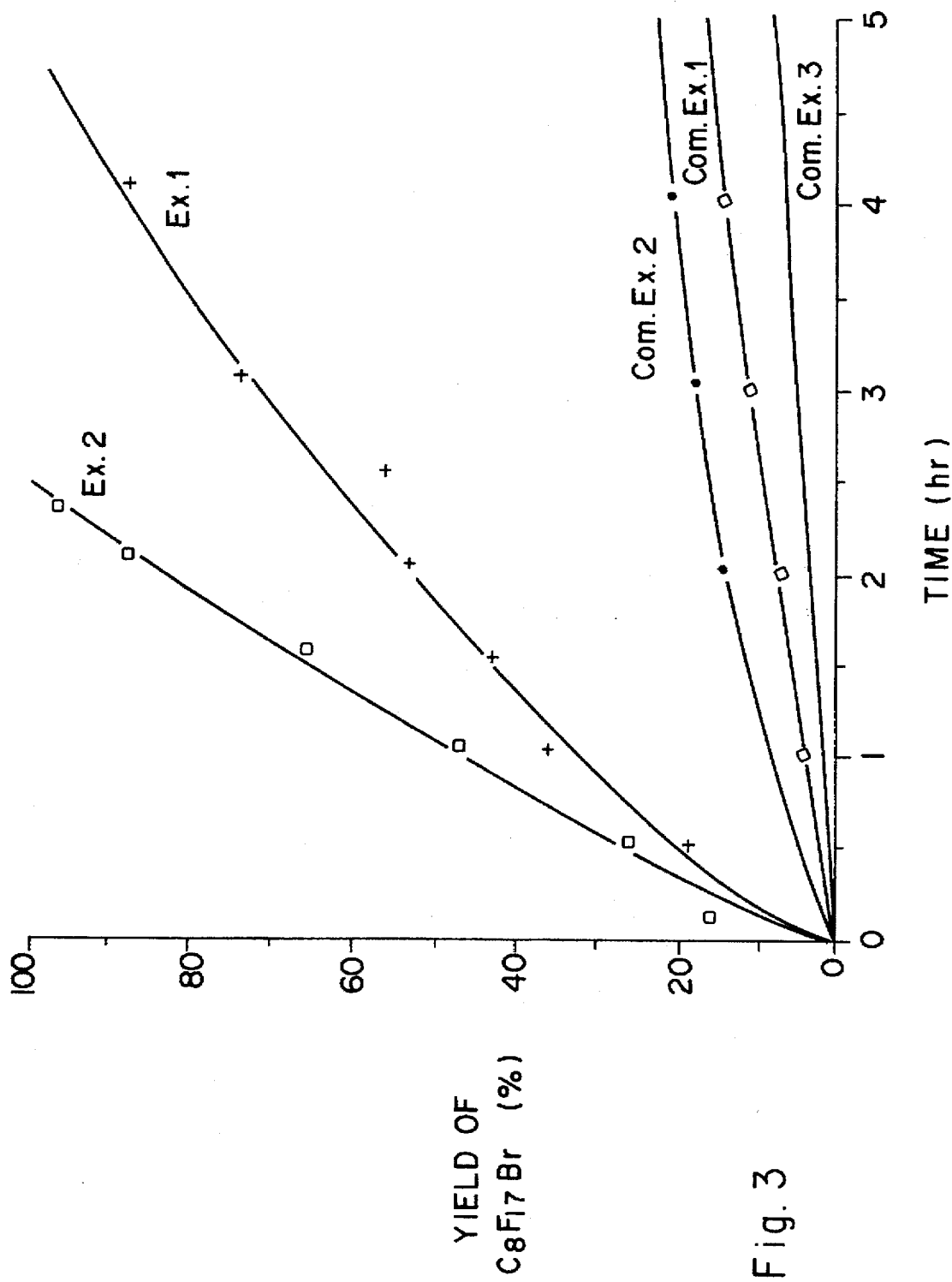
FIG. 3 is a graph showing the yields of $C_8F_{17}Br$ with time achieved in Examples 1 and 2, and Comparative Examples 1 to 3.

FIG. 3 shows the yields of $C_8F_{17}Br$ achieved with time in Examples 1 and 2, and Comparative Examples 1 to 3.

INDUSTRIAL APPLICABILITY

The invention makes it possible to industrially advantageously prepare a perfluoroalkyl bromide efficiently within a short period of time and in a high yield under such a mild heating condition as to permit reflux of a perfluoroalkyl iodide without using any additive.

We claim:
1. A process for preparing a perfluoroalkyl bromide comprising reacting a perfluoroalkyl iodide represented by the formula $C_nF_{2n+1}I$ wherein n is an integer of 6 to 10 with bromine in a light-transmitting reactor with exposure to light and heating at 120° to 180° C. while simultaneously removing IBr resulting as a by-product by separation of a layer.

2. A process for preparing a perfluoroalkyl bromide as defined in claim 1 wherein the reactor has a reflux tube provided at a lower portion thereof with a trap for separating said layer, and said IBr separating as a lower layer in the trap is removed.

3. A process for preparing a perfluoroalkyl bromide as defined in claim 1 wherein the perfluoroalkyl iodide is represented by the formula $C_nF_{2n+1}I$ wherein n is an integer of 6 to 8.

4. A process for preparing a perfluoroalkyl bromide as defined in claim 1 wherein about 1 to about 3 moles of the bromine is reacted with 1 mole of the perfluoroalkyl iodide.

5. A process for preparing a perfluoroalkyl bromide as defined in claim 1 wherein said heating is conducted at a temperature in the range of from 140° to 160° C.

* * * * *